United States Patent
Wahl et al.

(10) Patent No.: US 6,312,585 B1
(45) Date of Patent: Nov. 6, 2001

(54) METHOD FOR DETERMINING OXIDIZABLE CONSTITUENTS IN A GASEOUS MIXTURE

(75) Inventors: Thomas Wahl, Pforzheim; Thomas Brinz, Sindelfingen; Bernd Schumann, Rutesheim, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/269,948

(22) PCT Filed: Aug. 6, 1998

(86) PCT No.: PCT/DE98/02261

§ 371 Date: Jul. 6, 1999

§ 102(e) Date: Jul. 6, 1999

(87) PCT Pub. No.: WO99/08100

PCT Pub. Date: Feb. 18, 1999

(30) Foreign Application Priority Data

Aug. 12, 1997 (DE) .............................. 197 34 860

(51) Int. Cl.$^7$ ...................... G01N 27/406; G01N 27/407
(52) U.S. Cl. ...................... 205/783.5; 205/780.5; 205/781; 205/786.5; 205/787; 204/425
(58) Field of Search ................ 204/424–429; 205/781, 784, 785, 787, 783.5, 786.5, 780.5

(56) References Cited

U.S. PATENT DOCUMENTS

| 4,226,692 | 10/1980 | Isenberg . | |
|---|---|---|---|
| 4,505,783 | 3/1985 | Mase et al. . | |
| 4,718,991 | 1/1988 | Yamazoe et al. . | |
| 4,851,088 | * 7/1989 | Chandrasekhar et al. | 204/412 |
| 5,198,771 | * 3/1993 | Fidler et al. | 204/406 |
| 5,711,861 | * 1/1998 | Ward et al. | 204/403 |
| 5,879,525 | * 3/1999 | Kato | 204/424 |
| 6,019,881 | * 2/2000 | Kurosawa et al. | 204/424 |
| 6,083,370 | * 7/2000 | Kato et al. | 204/425 |

FOREIGN PATENT DOCUMENTS

96/28722 * 9/1996 (WO) .

OTHER PUBLICATIONS

Demitras et al., Inorganic Chemistry, ISBN:0134663594, pp. 208–210, 1972 Month unknown.*

Logothetis et al "High Temperature Oxygen Sensors Based on Electrochemical Oxygen Pumping", ACS Symposium Series 309, pp. 136–154, 1986.*

* cited by examiner

Primary Examiner—Jill Warden
Assistant Examiner—Kaj K. Olsen
(74) Attorney, Agent, or Firm—Kenyon & Kenyon

(57) ABSTRACT

A method and arrangement is described for determining oxidizable constituents in a gas mixture by using a solid electrolyte cell with at least one reference electrode and at least one working electrode made of electrically conducting mixed oxides which is sensitive to the oxidizable constituents, with the current between the reference electrode and the working electrode induced by electrochemical oxidation of a gas constituent to be determined being measured.

18 Claims, 1 Drawing Sheet

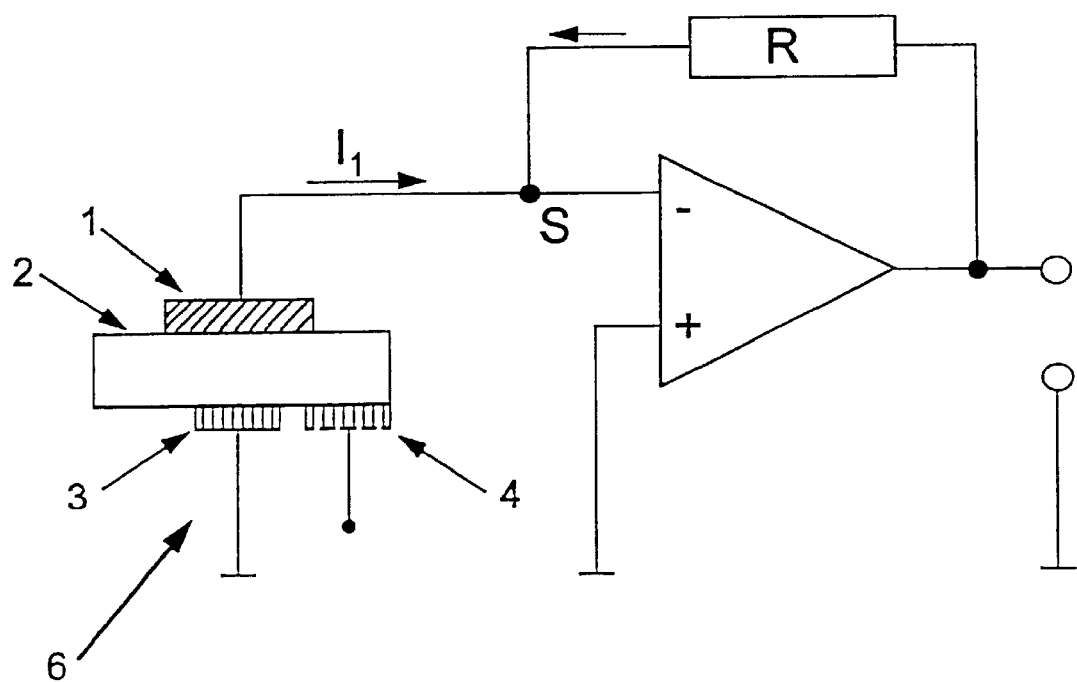

METHOD FOR DETERMINING OXIDIZABLE CONSTITUENTS IN A GASEOUS MIXTURE

FIELD OF THE INVENTION

The present invention relates to a method of determining oxidizable constituents in a gas mixture.

BACKGROUND INFORMATION

Methods of determining oxidizable constituents in gas mixtures are known. The conventional method is to measure a voltage between a working electrode and a reference electrode, which then permits an inference regarding the concentration of the gas constituent to be determined. Moreover, in the field of oxygen sensors for example, also known as lambda probes, it is known that the limit current induced between a reference electrode and a working electrode by transporting oxygen anions through a solid electrolyte body can be measured, permitting a determination of the equilibrium partial pressure concentration of oxygen according to the Nernst equation. The gases ($O_2$, NO) to be measured pass through a diffusion barrier and are pumped out by electrochemical forces at the working electrode. However, there is not yet any satisfactory method of determining individual combustible gas constituents in gas mixtures with sufficient accuracy. In the case of ammonia in particular, there are no reliable systems at the present. Cross sensitivity to various gas constituents also has not been minimized satisfactorily. Another problem so far has been the temperature control of such sensors, which has previously required various complicated measurement arrangements.

SUMMARY OF THE INVENTION

In comparison with the known related art, the method according to the present invention for determining oxidizable constituents in a gas mixture by using a solid electrolyte cell having at least one reference electrode and at least one working electrode which is sensitive to the oxidizable constituents has the advantage that it measures directly the current induced by electrochemical oxidation of a gas constituent to be determined. Since each gas constituent has a different electrochemical potential, a different current is also measured, the current depending on the concentration, so that each oxidizable gas constituent can be identified without any doubt and the concentration can be measured.

In a preferred embodiment, the working electrode is made of mixed metal oxides, which are electrically conducting and are selected from the group of spinels, pseudobrookites, eschynites and fergusonites. These classes of compounds permit a sufficient variation with regard to the sensitivity of the respective compound for specific gas constituents, such as NO, $NH_3$, unsaturated hydrocarbons or sulfur compounds. Satisfactory variation and sensitivity of the compounds for specific substances are guaranteed by this wide variety of compounds.

In another preferred embodiment, the temperature-dependent electrical conductivity of the solid electrolyte body is used for temperature control using the solid electrolyte cell. It is known that yttrium stabilized zirconium dioxide is electrically conductive in its cubic modification, with the conductivity being dependent on temperature. Due to this simple measurement of the electrical conductivity of the solid electrolyte body, the entire solid electrolyte cell can be used for temperature control of the combustion process without requiring complicated and expensive equipment.

In an advantageous manner, an a.c. voltage is applied to the reference electrode via the solid electrolyte body; the voltage is especially advantageously in the range of 0.1 to $10^6$ Hz, in particular in the range of 1 kHz to 200 kHz.

In a preferred embodiment, the voltage drop of the solid electrolyte cell is measured on a measuring shunt, and the resistance of the solid electrolyte body as a function of temperature is determined from the voltage drop, so that temperature control of the solid electrolyte cell is provided at all times due to the measurement of the voltage drop in the simplest possible manner.

BRIEF DESCRIPTION OF THE DRAWING

The FIGURE shows a circuit arrangement for implementing an exemplary embodiment of a method according to the present invention.

DETAILED DESCRIPTION

The sensor has a solid electrolyte 2, e.g., yttrium stabilized zirconium dioxide (YSZ) or some other oxygen ion conducting and electrically conducting material, a reference electrode 3, made of platinum, for example, or some other catalytically active noble metal. It is also possible to arrange additionally a second reference electrode 4 below the solid electrolyte body. Reference electrode 3 is exposed directly to the gas mixture, e.g., the exhaust gas of combustion engines, or it is exposed to the gas mixture through the porous solid electrolyte or through a diffusion layer incorporated into the solid electrolyte or at the side. If two reference electrodes 3, 4 are provided, one of the two reference electrodes may also be exposed to air. A metal oxide sensor layer 1 made of an electrically conducting spinel or an eschynite, for example, is arranged on solid electrolyte body 2. The spinel may be selected from the group of 2,3 spinels, 4,2 spinels or 6,1 spinels, for example. It is equally possible to use pseudobrookites. Examples of possible spinels include $NiFeMnO_4$, $CoCr_2O_4$, $CoCrMnO_4$, $TiCr_2O_5$, $TiCo_2O_4$, but this selection does not limit the invention in any way. Since each spinel is especially sensitive to a different oxidizable gas, it is now possible in an optimal manner to reliably determine even gases such as $NH_3$, which have previously been difficult to detect. The short-circuit current between metal oxide layer 1 and one of the reference electrodes 3 is measured for detection of oxidizable constituents. This is done with the circuit illustrated in the only figure.

A current is regulated by the operational amplifier across resistor R at point S, so that current $I_1$ coming from the sensor and current $I_R$ flowing across resistor R are equal and opposite. Point S is also known as virtual ground in this arrangement.

An additional second reference electrode 4 can be used for the temperature control of the sensor to the extent that the temperature dependence of the conductivity of the solid electrolyte is used. The conductivity of the solid electrolyte is measured by applying a low a.c. voltage to reference electrodes 3 and 4 across solid electrolyte 2, with the frequency of the voltage being between 0.1 and $10^6$ Hz, in particular from 1 kHz to 200 kHz and the amplitude being N=50 mV. Alternating current I is determined by measuring the voltage drop at a measuring shunt. The resistance of the solid electrolyte is determined from quotient U/I. The resistance of the solid electrolyte is a function of sensor temperature.

Hydrocarbons are oxidized electrochemically on the metal oxide electrode much as they are on a fuel cell. The present invention will now be explained in greater detail on the basis of a few examples for detection of gases according to their electrode reactions, although this selection of gases does not constitute a restriction in any way.

Oxygen:

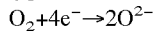

Nitrogen oxides ($NO_x$):
1. Oxidation of NO to $NO_2$: $NO+O^{2-} \rightarrow NO_2+2e^-$
2. Reduction of $NO_2$ to NO: $NO_2+2e^- \rightarrow NO+O^{2-}$
3. Reduction of NO: $NO+2e^- \rightarrow \frac{1}{2} N_2+O^{2-}$ $CO_x$:
1. Oxidation of CO to $CO_2$: $CO+O^{2-} \rightarrow CO_2+2e^-$
2. Reduction of $CO_2$ to CO: $CO_2+2e^- \rightarrow CO+O^{2-}$ $SO_x$:
1. Oxidation of $SO_2$: $SO_2+O^{2-} \rightarrow SO_3+2e^-$
2. Reduction of $SO_3$: $SO_3+2e^- \rightarrow SO_2+O^{2-}$
3. Reduction of $SO_2$: $SO_2+4e^- \rightarrow S+2\ O^{2-}$ $C_x H_y$:
$C_x H_y+(2x+y/2)\ O^{2-} \rightarrow x\ CO_2+y/2\ H_2O$ $NH_3$:
$2\ NH_3+3O^{2-} \rightarrow N_2+3H_2O$

What is claimed is:

1. A method for determining at least one oxidizable constituent in a gas mixture using a solid electrolyte cell, including a solid electrolyte body, at least one reference electrode and at least one working electrode, the at least one working electrode being composed of electrically conducting mixed oxides and being sensitive to the at least one oxidizable constituent, wherein the mixed oxides are mixed metal oxides which include at least one of pseudobrookites, eschynites and fergusonites, the method comprising the steps of:
   inducing a current, between the at least one reference electrode and the at least one working electrode, by an electrochemical oxidation of the at least one oxidizable constituent; and
   measuring the current.

2. The method according to claim 1, further comprising the step of:
   determining a temperature of the solid electrolyte cell using a temperature-dependent electrical conductivity of a solid electrode body of the solid electrolyte cell.

3. The method according to claim 2, further comprising the step of:
   applying an a.c. voltage through the solid electrolyte body to the at least one reference electrode, wherein the at least one reference electrode includes a first reference electrode and a second reference electrode.

4. The method according to claim 3, wherein the a.c. voltage is between 0.1 Hz and $10^6$ Hz.

5. The method according to claim 3, wherein the a.c. voltage is between 1 kHz to 200 kHz.

6. The method according to claim 3, wherein an amplitude of the a.c. voltage is 50 mV.

7. The method according to claim 1, wherein the solid electrolyte body includes at least one of an yttrium stabilized zirconium oxide and an oxygen ion conducting material.

8. The method according to claim 1, wherein the mixed oxide is $TiCr_2O_5$.

9. An arrangement for determining at least one oxidizable constituent of a gas mixture, the arrangement comprising:
   a solid electrolyte body;
   at least one reference electrode; and
   at least one working electrode, wherein the at least one working electrode includes at least one metal oxide selected from the group of pseudobrookites, eschynites and fergusonites, and the at least one metal oxide is sensitive to the at least one oxidizable constituent,
      wherein a current is induceable between the at least one reference electrode and the at least one working electrode by an electrochemical oxidation of the at least one oxidizable constituent of the gas mixture.

10. The arrangement according to claim 9, wherein the solid electrolyte body includes at least one of an yttrium stabilized zirconium oxide and an oxygen ion conducting material.

11. The arrangement according to claim 9, wherein the at least one oxidizable constituent includes $NH_3$.

12. The arrangement according to claim 9, further comprising:
   an amplifier arrangement, wherein the working electrode is coupled to an input of the amplifier arrangement; and
   a feedback arrangement, wherein the feedback arrangement is coupled across the input and an output of the amplifier arrangement.

13. The arrangement according to claim 12, wherein:
   the amplifier arrangement includes an operational amplifier, and the input of the amplifier arrangement is an inverting input of the operational amplifier; and
   the feedback arrangement includes an impedance arrangement.

14. The arrangement according to claim 12, wherein:
   a first current is coupled from the working electrode to the input;
   a second current is coupled from the feedback arrangement to the input; and
   the amplifier arrangement regulates the first current and the second current so that a common coupling point among the working electrode, the feedback arrangement and the input of the amplifier arrangement is a virtual ground.

15. An arrangement for determining at least one oxidizable constituent of a gas mixture, the arrangement comprising:
   a solid electrolyte, wherein the solid electrolyte body includes at least one of an yttrium stabilized zirconium oxide and an oxygen ion conducting material;
   at least one reference electrode;
   at least one working electrode, wherein the at least one working electrode includes at least one metal oxide selected from at least one of pseudobrookites, eschynites and fergusonites, and the at least one metal oxide is sensitive to the at least one oxidizable constituent,
      wherein a current is induceable between the at least one reference electrode and the at least one working electrode by an electrochemical oxidation of the at least one oxidizable constituent of the gas mixture;
   an amplifier arrangement, wherein the working electrode is coupled to an input of the amplifier arrangement; and
   a feedback arrangement, wherein the feedback arrangement is coupled across the input and an output of the amplifier arrangement.

16. The arrangement according to claim 15, wherein:
   the amplifier arrangement includes an operational amplifier, and the input of the amplifier arrangement is an inverting input of the operational amplifier; and
   the feedback arrangement includes an impedance arrangement.

17. The arrangement according to claim 15, wherein:
   a first current is coupled from the working electrode to the input;
   a second current is coupled from the feedback arrangement to the input; and
   the amplifier arrangement regulates the first current and the second current so that a common coupling point among the working electrode, the feedback arrangement and the input of the amplifier arrangement is a virtual ground.

18. The method according to claim 15, wherein the mixed oxide is $TiCr_2O_5$.

* * * * *